United States Patent [19]

Jaffe

[11] 4,056,104
[45] Nov. 1, 1977

[54] ENDOTRACHEAL TUBE

[76] Inventor: Burton Jaffe, 22 Burnham Road, West Newton, Mass. 02165

[21] Appl. No.: 649,329

[22] Filed: Jan. 15, 1976

[51] Int. Cl.² .......................................... A61M 25/00
[52] U.S. Cl. .................................... 128/351; 128/208
[58] Field of Search ............................... 128/348–351, 128/206, 208

[56] References Cited

U.S. PATENT DOCUMENTS

| | | | |
|---|---|---|---|
| 3,363,629 | 1/1968 | Kuhn | 128/351 |
| 3,395,711 | 8/1968 | Plzak | 128/351 |
| 3,638,655 | 2/1972 | Doherty | 128/351 |
| 3,734,100 | 5/1973 | Walker et al. | 128/351 |
| 3,880,168 | 4/1975 | Berman | 128/351 |

FOREIGN PATENT DOCUMENTS 64,792  2/1913  Switzerland ................. 128/349 R Primary Examiner—Dalton L. Truluck
Attorney, Agent, or Firm—Wolf, Greenfield & Sacks

[57] ABSTRACT

The tube has a round cross-section along the majority of its length but includes a relatively short section that is of a triangular cross-section. This triangular cross-section is positioned along the tube to contact the larynx and matches the shape of the larynx. A cuff extends about the tube below the triangular cross-section area and a pilot tube is provided which connects via a cuff inflation lumen in the wall of the tube to the cuff.

11 Claims, 3 Drawing Figures

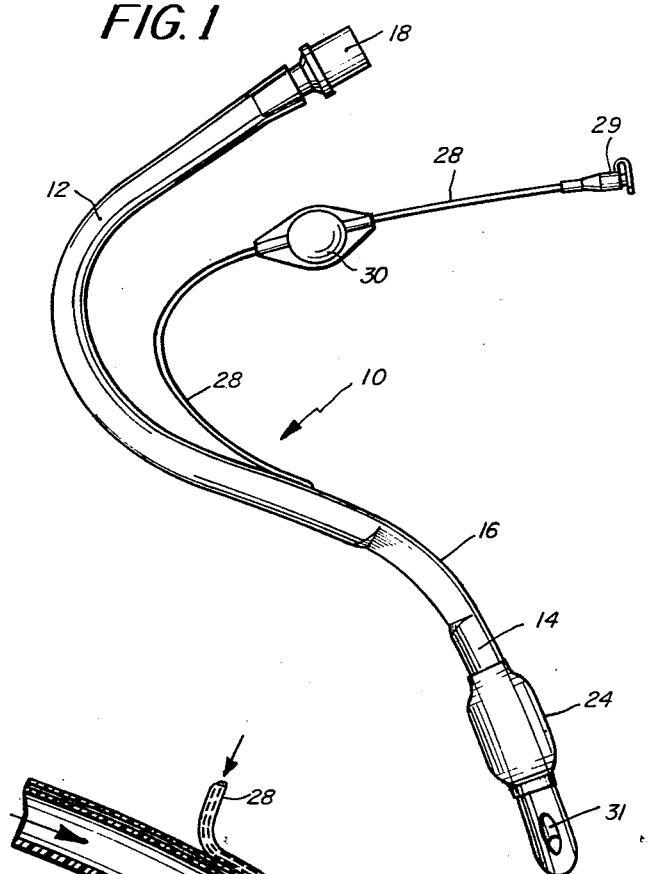
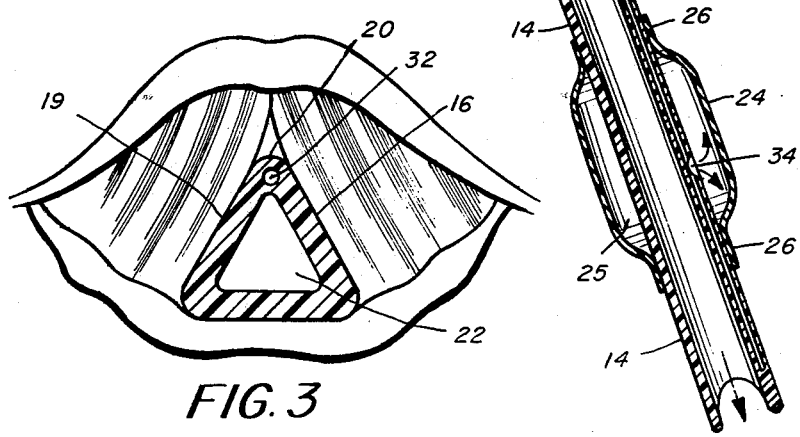

ENDOTRACHEAL TUBE

BACKGROUND OF THE INVENTION

The present invention relates in general to an endotracheal tube. More particularly, the present invention is concerned with an improved construction of an endotracheal tube for lessening the likelihood of tissue damage and infection in the area of the larynx and trachea. The endotracheal tube of this invention may be adapted for use either by adults or even a newborn.

Usually, persons including tiny infants are intubated with thin-walled round endotracheal tubes which may pass either through the nose or the mouth. Intubation can usually be tolerated for only a relatively short period of time and if the intubation exceeds say 72 hours there may be significant tissue damage to the larynx. In infants this tolerable time period may be somewhat longer but eventually damage will occur.

It is known that the endotracheal tube rests in the posterior commissure of the glottis. The continuous pressure and tube movement due to positive end expiratory pressure and head motion causes changes to occur in the tissue of this area. It has been found that ulceration and erosion of the medial surface of the arytenoid occurs. There also may be thickening and granulation tissue formation of the interarytenoid region. Following ulceration, granulation tissue and scarring or adhesions may occur to interfere with the normal speech or breathing of a person. Furthermore, laryngeal stenosis is a severe medical complication.

Studies have been made with children to determine the effect of intubation. They have found that there is a residual grooving defect of the vocal process, leaving an incomplete glottic closure. The children were asphonic or severely hoarse when the tube was removed.

It has been found that there are possibly a number of reasons for the laryngeal damage. The usual tube that is used is referred to as a Magill tube design having a gradual curving shape. This type of tube results in significant pressure on posterior commissure from the weight of the tongue resting on the tube. Also in the supine patient neck flexion increases the posterior coiling of the tube against the posterior glottis, while the stiffness of the tube wall makes it less likely to bend and conform to the natural curves of the hypopharynx and larynx which is a further source of pressure. Damage is also believed to occur because the tube is round, and yet the posterior commissure and arytenoid areas form a triangular space. This results in damage, especially to the vocal processes of the arytenoids in the midline of a posterior commissure.

Although a tube which is small enough to pass easily through the glottis decreased the pressure, positive pressure ventilation is more effective if a fairly tight seal is created at the glottis. However, if a larger tube is used there is then an increased possibility of irritation and ulceration.

Accordingly, one object of the present invention is to provide an improved construction for an endotracheal tube.

Another object of the present invention is to provide an endotracheal tube that is constructed to reduce or eliminate ulcerations of the larynx.

A further object of the present invention is to provide an endotracheal tube that has a modified cross-sectional shape to more easily conform to the larynx.

Still a further object of the present invention is to provide an endotracheal tube having a cuff disposed at the distal end of the tube and including means for expanding the cuff after the tube has been inserted in the patient.

Still another object of the present invention is to provide an endotracheal tube having an S-shaped configuration.

SUMMARY OF THE INVENTION

To accomplish the foregoing and other objects of this invention, there is provided an endotracheal tube that has a round cross section along the majority of its length but includes limited length section having a triangular cross-section. This triangular section of the tube is shaped to comform to the larynx of a human and disposed along the tube preferably nearer to the distal end of the tube so that this section contacts the larynx when the tube is properly inserted in place in the patient. The tube is constructed of a plastic material but is pliable. The tube may be constructed in an arcuate shape or it has been found that damage in some instances may be reduced by using an S-shaped tube. The tube may be constructed in different sizes depending upon whether use is being made with an adult or a newborn. The triangular cross section is preferably formed by substantially straight outer walls which may be slightly rounded where the walls meet. A cuff may be disposed at the distal end of the tube below the triangular cross-sectional area and a pilot tube couples via a lumen disposed in the wall of the tube to the cuff. Means may be provided for passing air via the pilot tube and lumen to the cuff for causing expansion thereof.

BRIEF DESCRIPTION OF THE DRAWINGS

Numerous other objects, features and advantages of the invention should now become apparent upon a reading of the following detailed description taken in conjunction with the accompanying drawings, in which:

FIG. 1 is an elevational view of one embodiment of the device of this invention;

FIG. 2 is a cross-sectional view showing in detail a segment of the endotracheal tube shown in FIG. 1; and FIG. 3 is a cross-sectional view taken along line 3—3 of FIG. 2 with the tube inserted in a patient.

DETAILED DESCRIPTION

FIG. 1 shows the endotracheal tube 10 including a top round section 12, a bottom round section 14, with sections 12 and 14 being interconnected by section 16 which has a triangular cross-section. An adapter 18 may be disposed at the top end of the tube. The adapter 18 may or may not be used depending upon the medical condition of the patient. The tube 10 may be constructed of a plastic material that is not completely hard but it is pliable.

FIG. 3 is a cross-sectional view taken along line 3—3 of FIG. 2 and shows clearly the triangular shape of the section 16 including the substantially flat walls 19 and the rounded corners 20. The entire tube defines a passageway 22 which has a round cross-section throughout sections 12 and 14 and may have a round or preferably a triangular cross-section as shown in FIG. 3 through the section 16. FIG. 3 shows the tube in a patient and it is noted that the triangular cross-section conforms to the shape of the larynx. Further, this triangular cross-section is positioned nearer to the distal end of the endotracheal tube so that when the tube is in position in the patient the proper section of the tube with the triangular cross-section will be in contact with the larynx.

A cuff 24 which may be constructed of a soft plastic material is affixed to the endotracheal tube at the distal end thereof just below the section 16. FIG. 2 clearly shows in a cross-sectional view the cuff 24 which may be constructed of a relatively soft pliable material such as a plastic. At the ends 26 of the cuff 24 the cuff is affixed to the tube. The cuff 24 forms a chamber 25 and when the tube is inserted in the patient the cuff is expanded.

As indicated in FIG. 1 there is also provided a pilot tube 28 which connects from an adapter 29 by way of a pressure device 30 to the lumen 32 in the wall of the tube. The end of the lumen 32 terminates in the port 34 which communicates with the chamber 25 of the cuff 24. FIG. 3 also shows the lumen 32 which is of a round cross-section. Similarly, this lumen could have a triangular cross-section.

Having described one embodiment of the present invention, it should now become apparent to one skilled in the art that numerous other embodiments and modifications of the one shown herein are contemplated, all of which should fall within the scope of the present invention. For example, the tube may have an arcuate shape but it is preferred that the tube have an S-shape thus reducing posterior laryngeal pressure. The only problem with using the S-shaped tube is that a stylet is needed for insertion. The length of the section 16 may vary. For tubes used with children this length may be on the order of two centimeters. For tubes used with adults the length may be in the range of 2-5 centimeters.

What is claimed is:

1. An endotracheal tube comprising a pliable hollow plastic tube of a length many times its width having open distal and proximate ends defining a fluid passageway, a section of the tube spaced from either end having a triangular cross-section extending along at least a portion of the tube that would normally contact the larynx and conforming to the shape of the larynx when the tube is in position with the distal end of the tube in the trachea and the proximate end extending from the mouth, a cuff coaxial with and secured to the tube between the distal end and said section, and a cuff inflation lumen extending longitudinally from said cuff lengthwise of the wall of said section toward said proximate end, said section having a substantially uniform wall thickness along its length extending along the tube a distance less than the entire length of the tube with the passageway through said section also having a triangular shape to optimize fluid passage through the tube.

2. An endotracheal tube as set forth in claim 1 wherein said triangular section is defined by three straight walls integrally connected by rounded edges.

3. An endotracheal tube as set forth in claim 2 wherein said tube has an S-shape.

4. An endotracheal tube as set forth in claim 1 including a hole in the wall of the tube at the distal end for permitting air passage should the end of the tube become blocked.

5. An endotracheal tube as set forth in claim 4 including a pilot tube and pressure means in the pilot tube, said pilot tube coupling to the lumen.

6. An endotracheal tube as set forth in claim 1 wherein said cuff is spaced from but adjacent one end of said triangular section.

7. An endotracheal tube as set forth in claim 1 wherein said lumen extends through said section at one of the edges defining the triangular section.

8. An endotracheal tube as set forth in claim 1 wherein said section has a length at least on the order of 2 centimeters with the remainder of the tube being of rounded shape.

9. An endotracheal tube as set forth in claim 8 wherein said section has a length on the order of 2-5 centimeters.

10. An endotracheal tube as set forth in claim 1 wherein said triangular section is formed by three contiguous planar wall segments.

11. An endotracheal tube as set forth in claim 1 wherein said section has a length only as long as the length of the larynx with the remainder of the tube being of rounded shape.

* * * * *